United States Patent [19]

Schlager

[11] Patent Number: 5,017,586

[45] Date of Patent: May 21, 1991

[54] 5-DIALKYLAMINOMETHYL-2-FURANOMETHANOL DERIVATIVES HAVING ANTI-HYPERTENSIVE PROPERTIES

[75] Inventor: Ludwig H. Schlager, Vienna, Austria

[73] Assignee: Gerot-Pharmazeutika Gesellschaft m.b.H., Vienna, Austria

[21] Appl. No.: 350,878

[22] Filed: May 12, 1989

[30] Foreign Application Priority Data

May 13, 1988 [AT] Austria ................................ 1245/88

[51] Int. Cl.$^5$ ................. C07D 401/13; C07D 405/12; C07D 405/14; A61K 31/435
[52] U.S. Cl. ..................................... 514/318; 514/336; 514/343; 546/194; 546/281; 546/283; 544/55; 544/58.5; 544/63; 544/96; 544/124; 544/360
[58] Field of Search ...................... 546/283, 194, 281; 514/336, 222.2, 226.8, 227.8, 228.8, 231.5, 247, 249, 318, 343; 544/55, 58.5, 63, 96, 124, 360

[56] References Cited

FOREIGN PATENT DOCUMENTS 0068171 1/1983 European Pat. Off. ............ 546/321
0194906 9/1986 European Pat. Off. ............ 546/321
2003148 7/1971 Fed. Rep. of Germany ...... 546/321

OTHER PUBLICATIONS

Chemical Abstracts; 70:875080f; 1969.
Chemical Abstracts; 84:17090m; 1976.
Chemical Abstracts; 98:215490u; 1983.
Chemical Abstracts; 101:110746j; 1984.
Chemical Abstracts; 101:151862n; 1984.

Primary Examiner—Alan L. Rotman

Attorney, Agent, or Firm—Sughrue,Mion,Zinn,Macpeak & Seas

[57] ABSTRACT

Derivatives of 5-aminomethyl-2-furanomethanol represented by formula (I), or pharmaceutically acceptable salts thereof, which possess calcium-antagonistic activity and are effective in lowering blood pressure, and a process for preparing and using the same:

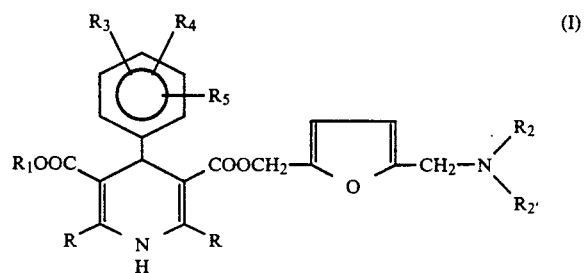

wherein R, $R_1$, $R_2$ and $R_2'$ each represent a lower alkyl group containing 1 to 4 carbon atoms, with the proviso that $R_2$ and $R_2'$, together with N, may form a 5- or 6-membered saturated heterocyclic ring which may contain an additional heteroatom, selected from the group consisting of as O, N and S, or $R_2'$ represents an aralkyl group;

wherein $R_3$ and $R_4$ are each selected from the group consisting of a hydrogen atom, a halogen, a nitro group and a methoxy group; and wherein $R_5$ is selected from the group consisting of a halogen, a difluoromethoxy group, a trifluoromethyl group, a nitro group, a carbamylmethoxy group, a cyanomethoxy group and a mesyloxy group.

5 Claims, No Drawings

5-DIALKYLAMINOMETHYL-2-FURANOMETHANOL DERIVATIVES HAVING ANTI-HYPERTENSIVE PROPERTIES

FIELD OF THE INVENTION

The present invention relates to derivatives of 5-dialkylaminomethyl-2-furanomethanol, a method for the preparation of the same and a method for use of the same.

BACKGROUND OF THE INVENTION 5-dialkylaminomethyl-2- furanomethanol, which is represented by formula (A) below, has been known since 1947.

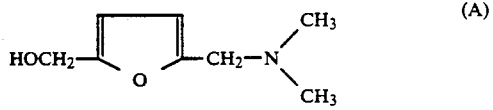

The above compound represented by formula (A) has only been used since 1976 for the synthesis of antiulcer drugs, due to the discovery of the antiulcer drug ranitidine. In most cases, the use of the compound represented by formula (A) above has been limited to the preparation of the corresponding furanomethyl thioethers.

Heretofore, among esters of the compound represented by formula (A), only those of sulfuric acid have been known. These compounds are known to be useful as antiulcer drugs.

Prior to the present invention there was no teaching or suggestion that such compounds would be effective on blood circulation, i.e., to have calcium-antagonistic and antihypertensive properties Although 1, 4-dihydropyridine-3, 5-dicarboxylic esters containing furano rings in the ester radical are known (Chem. Abstr. 75:151587d; and Chem. Abstr. 100:85591z), esters having the substituents shown in the compound represented by (A) have not been known.

SUMMARY OF THE INVENTION

Accordingly, an object of the present invention is to provide novel derivatives of 5-dialkylaminomethyl-2-furanomethanol useful as calcium-antagonists and in lowering blood pressure.

Another object of the present invention is to provide a method for preparing the novel derivatives.

Still another object of the present invention is to provide a method for using the novel derivatives.

In one embodiment, the above-described objects have been met by derivatives of 5-dialkylaminomethyl-2-furanomethanol represented by general formula (I), and pharmaceutically acceptable salts thereof:

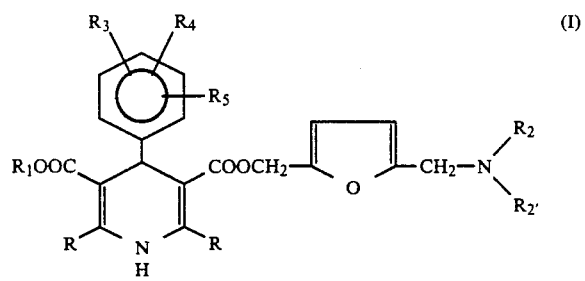

wherein R, $R_1$, $R_2$ and $R_2'$ each represent a lower alkyl group containing 1 to 4 carbon atoms, with the proviso that $R_2$ and $R_2'$, together with N, may form a 5- or 6-membered saturated heterocyclic ring which may contain an additional heteroatom, selected from the group consisting of as O, N and S, or $R_2$ represents an aralkyl group with 7 to 12 C-atoms;

wherein $R_3$ and $R_4$ are each selected from the group consisting of a hydrogen atom, a halogen, a nitro group and a methoxy group; and wherein $R_5$ is selected from the group consisting of a halogen, a difluoromethoxy group, a trifluoromethyl group, a nitro group, a carbamylmethoxy group, a cyanomethoxy group and a mesyloxy group.

In another embodiment, the above-described objects of the present invention have been met by a process comprising:

(A) reacting a derivative of 5-aminomethyl-2-furanomethanol represented by general formula (II):

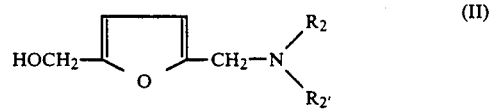

wherein $R_2$ and $R_2'$ are as defined above, with a diketene or the acetone adduct thereof, (B) condensing the resulting 2-acetoacetoxymethyl compound represented by general formula (III):

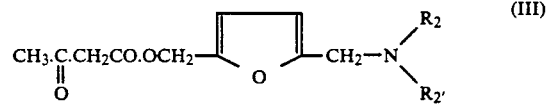

with a substituted benzaldehyde, and (C) cyclizing the resulting reaction product with an ester of 3-aminocrotonic acid so as to yield the compound represented by general formula (I).

In a third embodiment, the above-described objects have been met by method for lowering blood pressure comprising administering a pharmaceutically effective amount of a compound represented by general formula (I).

DETAILED DESCRIPTION OF THE INVENTION

The process of the present invention is preferably carried out in the presence of a catalyst, e.g., piperidine acetate, with a substituted benzaldehyde and with separation of water.

The compounds represented by general formula (I) may be administered either alone or together with pharmaceutically acceptable carriers for the treatment of hypertension.

Galenic processing of the compounds represented by general formula (I) into tablets, capsules solutions, suspensions or suppositories can be carried out as appropriate using additives well known in the art.

For lowering the blood pressure of hypertensive individuals, the dosage is adapted to the existing high blood pressure and it is started from relatively small doses. Generally, 1 to 100 mg of the compound represented by general formula (I) will be sufficient per one application.

The following examples are provided for illustrative purposes only and are in no way intended to limit the scope of the present invention.

EXAMPLE 1

5-dimethylaminomethyl-2-acetoacetoxy methyl furan, used as a starting material was prepared as follows:

89 g of freshly distilled 5-dimethylaminomethyl-2-furanomethanol and 84.6 g of diketene acetone adduct were heated under reflux in 80 ml of toluene for 1 hour. The gradually released acetone was allowed to distill off. To the resulting residue was added ethyl acetate and the solution was purified over a column of silicagel 60. The oil remaining after evaporation of the eluate consisted of 5-dimethylaminomethyl-2-acetoacetoxymethyl furan.

Next, a mixture of 54.7 g of 5-dimethylaminomethyl-2-acetoacetoxymethyl furan and 40 g of 2 3-dichlorobenzaldehyde was heated, after the addition of 8 drops of each of glacial acetic acid and piperidine, in 200 ml of dry methylene chloride under a water separator, until the formation of water ceased. The reaction mixture was then filtered using activated charcoal and Celite, and the resulting filtrate was subjected to evaporation.

The resulting residue was heated under reflux, with 26.3 g of the methyl ester of 3-aminocrotonic acid, in 150 ml of absolute ethanol. To the resulting evaporation residue was added 50 ml of ethyl acetate and purified by column chromatography using 300 g of silicagel 60 and ethyl acetate as the eluant. The purified fraction was subjected to evaporation, and the resulting oil was dissolved in acetone and acidified with alcoholic HCl. The precipitated crude product was further purified by boiling with isopropyl ether and recrystallized from acetone.

The resulting hydrochloride of 2, 6-dimethyl-3-(5-dimethyl-amino-methyl-furano-2-methoxy-carbonyl)-4-(2, 3-dichlorophenyl)-5-methoxy melting point of 189°–191° C.

EXAMPLE 2

2.7 g of the starting material obtained as in Example 1 (formula III, $R_2$ and $R_2$=methyl) was heated under reflux in 80 ml of absolute benzene in the presence of 0.3 g of piperidine acetate and 2 0 g of 2-carbamylmethoxy benzaldehyde and water was separated. After 2 hours, the reaction mixture was subjected to evaporation. To the resulting residue was added 20 ml of absolute methanol. Next, 1.3 g of the methyl ester of 3-aminocrotonic acid was added and heated under reflux for an additional 1½ hours. Then, the residue was subjected to evaporation, washed with ethyl acetate and water, and the organic solution was extracted with 2.0 N acetic acid. The aqueous phase was neutralized with dilute NaOH and extracted with ethyl acetate. After subjecting the resulting solution to evaporation, the crude product remained as an orange colored oil which was purified by column chromatography on silicagel 60 using acetone as the eluant. The resulting product. 2, 6-dimethyl-3 -(5-dimethylamino-methylfurano-2-methoxycarbonyl)-4-(2-carbamylmethoxyphenyl)-5-methoxycarbonyl-1, 4-dihydropyridine, was recrystallized from cold ethyl acetate in the form of the base having a melting point of 174°–175° C.

EXAMPLE 3

The starting material obtained as in Example 1 (formula (III), $R_2$ and $R_2$=methyl) was reacted with 2-chlorobenzaldehyde as in Example 1 so as to obtain 2, 6-dimethyl-3-(5-dimethylamino-methylfurano-2-methoxycarbonyl)-4-(2-chlorophenyl)-5-methoxycarbonyl-1, 4-dihydropyridine in form of the base having a melting point of 154°–156° C.

EXAMPLE 4

2-cyanomethoxy-3, 5-dibromobenzaldehyde, used as starting material, was prepared as follows:

6.43 g of a 30% methanolic solution of sodium methylate were added dropwise with stirring to a solution of 10 g of 3, 5-dibromosalicylic aldehyde in 100 ml of methanol. To the resulting evaporation residue of the phenolate solution was added 50 ml of dimethylformamide. Next. 2.68 g of chloroacetonitrile. 1.0 g of triethylbenzyl ammonium chloride and 1.0 g of potassium iodide was added and the resulting solution was heated for 5 hours at 40° C. Then, the mixture was evaporated in vacuo. To the resulting residue was added ethyl acetate, the solution was extracted successively with water, 1.0 N NaOH, 1.0 N HCl and water and filtered after the addition of activated charcoal. Finally, the filtrate was subjected to evaporation. Upon boiling the crude product in isopropyl ether, 2-cyanomethoxy-3, 5-dibromobenzaldehyde was obtained as a brownish powder having a melting point of 125°–130° C.

The procedures of Examples 1 and 2 were repeated except the above salicylic aldehyde derivative was used instead of the benzaldehyde compounds used in Examples 1 and 2. As a result, 2, 6-dimethyl-3 -(5-dimethylamino-methylfurano-2-methoxycarbonyl)-4-(2-cyanomethoxy-3, 5-dibromophenyl)-5-methoxycarbonyl-1, 4-dihydropyridine, having a melting point of 145°–150° C., was obtained.

EXAMPLE 5

2-(N-diphenylmethylcarbamylmethoxy)-benzaldehyde used as starting material, was prepared as follows:

2.08 g of a 30% methanolic solution of sodium methylate are added to a solution of 1.41 g of salicylic aldehyde in 10 ml of methanol. To the resulting evaporation residue was added 25 ml of absolute n-propanol and stirred with 3.0 g of N-(diphenylmethyl)-chloroacetamide (m.p. 131°–134° C.; obtained from the reaction of α-aminodiphenylmethane and chloroacetyl chloride in ethyl acetate/NaHCO$_3$) for 12 hours under reflux. After evaporation of the solvent, the residue was dissolved in hot ethyl acetate, filtered and the cold filtrate was diluted with isopropyl ether. When allowed to stand in the cold, the resulting 2-(N-diphenylmethylcarbamylmethoxy)-benzaldehyde, which melts at 110°–113° C. crystallized.

Upon reacting the above aldehyde using the procedures described in Examples 1 and 2, 2, 6-dimethyl-3-(5-dimethylaminomethylfurano-2-methoxycarbonyl)-4-[2-

(N-diphenylmethlycarbamylmethoxy)-phenyl]-5- methoxycarbonyl-1, 4-dihydropyridine, having a melting point of 163°–164° C., was obtained.

EXAMPLE 6

5.0 g of 5-(piperidinomethyl)-furfuryl alcohol (*Chem Abstr.* 69:59003f (1968)) were heated under reflux with 3.8 g of diketene acetone adduct in 20 ml of absolute toluene until all of the acetone had evaporated. Upon subjecting the reaction mixture to evaporation in vacuo, an orange colored oil was obtained consisting of 2-acetoacetoxy-methyl-5-piperidinomethyl furan.

3.1 g of the resulting oil were heated under reflux together with 2.0 g of 2-carbamylmethoxybenzaldehyde in 80 ml of absolute benzene, along with 2 drops of each of glacial acetic acid and piperidine, for about 2 hours and water was separated. Then, the residue was subjected to evaporation and dissolved in 20 ml of absolute methanol and stirred for about 2 hours under reflux after the addition of 1.3 g of the methyl ester of 3-aminocrotonic acid.

The course of the condensation and cyclization reaction was followed using a thin layer chromatogram (silicagel 60 F 254, using chloroform/methanol (9:1) as the eluant).

After completion of the reaction, the solvent was distilled off, and to the residue was added ethyl acetate. Then, the solution was extracted successively with water and 5.0 N HCl Next, the acid extract was neutralized with 5.0 N NaOH and the mixture was reextracted with ethyl acetate. After drying (with $Na_2SO_4$) and evaporating the organic solution, a yellow residue remained. After recrystallization from acetone, 2, 6-dimethyl-3-(5-piperidinomethylfurano-2-methoxycarbonyl)- 4-(2-carbamymethoxyphenyl)-5-methoxycarbonyl-1, 4-dihydropyridine, having a melting point of 180°–182° C., was obtained.

Using the procedures described in Examples 1 to 6, the following additional derivatives represented by general formula (I) were obtained.

| R | $R_1$ | $NR_2R_{2'}$ | $R_3$ | $R_4$ | $R_5$ | m.p. °C. (base/salt) |
|---|---|---|---|---|---|---|
| $CH_3$ | $CH_3$ | $N(CH_3)_2$ | H | H | 2-O,$SO_2CH_3$ | 100–105 (.HCl) |
| $CH_3$ | $CH_3$ | piperidino | H | H | 2-F | 150–153 (base) |
| $CH_3$ | $CH_3$ | $N(CH_3)_2$ | H | H | 2-$CF_3$ | 116–118 (base) |
| $CH_3$ | $CH_3$ | $N(CH_3)_2$ | H | H | 2-O,$CH_2CON(CH_3)_2$ | 109–113 (.HCl) |
| $CH_3$ | $CH_3$ | $N(CH_3)_2$ | H | H | 2-$NO_2$ | 106–108 (base) |
| $CH_3$ | $CH_3$ | piperidino | H | 3-Cl | 2-Cl | 84–85 (base) |
| $CH_3$ | $CH_3$ | $N(CH_3)_2$ | H | H | 2-O,$CH_2CO$,morpholino | 147–155 (base) |
| $CH_3$ | $CH_3$ | piperidino | H | H | 2-Cl | 137 (base) |
| $CH_3$ | $CH_3$ | piperidino | H | H | 2-$CF_3$ | 152–155 (base) |
| $CH_3$ | $CH_3$ | piperazino-phenyl-$OCH_3$ | H | H | 2-O,$CH_2CONH_2$ | 170–175 (base) |
| $CH_3$ | $CH_3$ | morpholino | H | H | 2-O,$CH_2CONH_2$ | 179–180 (base) |

-continued

| R | R$_1$ | N(R$_2$)(R$_2'$) | R$_3$ | R$_4$ | R$_5$ | m.p. °C. (base/salt) |
|---|---|---|---|---|---|---|
| CH$_3$ | CH$_3$ | N(C$_2$H$_5$)$_2$ | H | H | 2-O,CH$_2$CONH$_2$ | 152–153 (base) |
| CH$_3$ | CH$_3$ | N(CH$_3$)$_2$ | 4-F | H | 2-F | 111–113 (base) |
| CH$_3$ | CH$_3$ | piperazinyl-(2-methoxyphenyl) | H | H | 3-NO$_2$ | 141–143 (base) |
| CH$_3$ | CH$_3$ | N(CH$_3$)$_2$ | H | H | 3-NO$_2$ | 136–138 (base) |
| CH$_3$ | CH$_3$ | piperazinyl-(2-methoxyphenyl) | H | 3-Cl | 2-Cl | 144–146 (base) |
| CH$_3$ | CH$_3$ | piperazinyl-(2-methoxyphenyl) | H | H | 2-F | 117–120 (base) |
| CH$_3$ | CH$_3$ | piperazinyl-(4-fluorophenyl) | H | H | 2-OCH$_2$CONH$_2$ | >200 (dec.) (base) |
| CH$_3$ | CH$_3$ | piperidinyl | H | H | 2-O,SO$_2$CH$_3$ | 95–101 (.HCl) |
| CH$_3$ | CH$_3$ | piperazinyl-(2-CF$_3$-phenyl) | H | H | 2-O,CH$_2$CONH$_2$ | 185–190 (base) |
| CH$_3$ | CH$_3$ | morpholinyl | H | H | 2-F | 169–171 (base) |
| CH$_3$ | CH$_3$ | N(CH$_3$)$_2$ | H | H | 2-F | 103–105 (base) |
| CH$_3$ | CH$_3$ | piperidinyl-(benzimidazolinon-yl) | H | H | 2-Cl | 95–118 (base) |

EXAMPLE 7

5-[4-(2-methoxyphenyl)-piperazino-methyl]-furfuryl alcohol, used as an intermediate, was prepared by Mannich condensation as follows:

A mixture of 30 g of furfuryl alcohol, 70 g of N-(2-methoxy-phenyl)-piperazine hydrochloride and 23 g of paraformaldehyde was stirred in 200 ml of ethanol for 12 hours under reflux and then evaporated in vacuo. Next, the residue was diluted with a small amount of water. The concentrate was made alkaline by the addition of NaOH and then repeatedly extracted with diethyl ether. Next, the ether solution was treated with activated charcoal and $Na_2SO_4$ as discussed above, filtered and evaporated. A solution of the residue in ethyl acetate was purified by column chromatography with silicagel 60. After evaporation, the pure fraction yielded an oil, which crystallized if it was allowed to stand. After washing with diisopropyl ether, a powder having a melting point of 97°–99° C. was obtained.

EXAMPLE 8

5-[4-(2-oxo-1-benzimidazolinyl)-piperdino-methyl]-2-furano-methanol, used as an intermediate, was prepared as in Example 7 by Mannich condensation of 4-(2-oxo-1-benzimidazolinyl)-piperidine hydrochloride, furfuryl alcohol and paraformadehyde in boiling ethanol. The intermediate melted, after purification over a column of silicagel 60, at 73° C.

In order to determine the pharmacological usefulness of the compounds represented by general formula (I), the acute toxicity of the hydrochloride of the compound represented by formula (A) was tested. This is because the hydrochloride may be formed upon metabolism of the compound represented by general formula (I). The hydrochloride has an $LD_{50}$ of 289 mg/kg (mouse. i.v.). thus demonstrating that the compound represented by formula (A) shows a very low toxicity.

The final product obtained in Example 1 showed a higher calcium-antagonism activity (tonus of the uterus of the rat in an organ bath) and lowering of the blood pressure of the rat, compared to the known preparations Nifedipine and Verapamile.

While the invention has been described in detail and with reference to specific embodiments thereof, it will be apparent to one skilled in the art that various changes and modifications can be made therein without departing from the spirit and scope thereof.

I claim:

1. A compound of formula (I), or a pharmaceutically acceptable salt thereof:

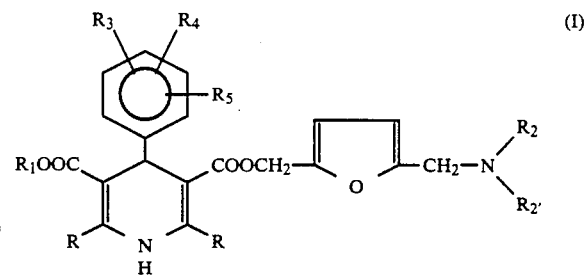

wherein R, $R_1$, $R_2$ and $R_2$ each represent a lower alkyl group containing 1 to 4 carbon atoms, or $R_2$ and $R_2'$, together with N, form a 5- or 6-membered saturated heterocyclic ring;

wherein $R_3$ and $R_4$ are each selected from the group consisting of a hydrogen atom, a halogen, a nitro group and a methoxy group; and wherein $R_5$ is selected from the group consisting of a halogen, a difluoromethoxy group, a trifluoromethyl group, a nitro group, a carbamylmethoxy group, a cyanomethoxy group and a mesyloxy group.

2. The compound as claimed in claim 1, wherein said heterocyclic ring is selected from the group consisting of pyrrolidino and piperidino, wherein said heterocyclic ring may be substituted by a lower alkyl on a carbon atom of said ring.

3. A method for lowering blood pressure comprising administering to a hypertensive subject a pharmaceutically effective amount of a compound claimed in claim 1.

4. The method as claimed in claim 3, wherein 1 to 100 mg of said compound is administered.

5. An antihypertensive composition comprising, as an active ingredient, a pharmaceutically effective amount of the compound of claim 1, and a pharmaceutically acceptable carrier or diluent.

* * * * *

UNITED STATES PATENT AND TRADEMARK OFFICE
CERTIFICATE OF CORRECTION

PATENT NO. : 5,017,586
DATED : May 21, 1991
INVENTOR(S) : Schlager

It is certified that error appears in the above-indentified patent and that said Letters Patent is hereby corrected as shown below:

On the title page: Item [30] Foreign Priority Data:
should be -- A1257/88 --.

Signed and Sealed this

Twenty-ninth Day of June, 1993

Attest:

MICHAEL K. KIRK

Attesting Officer

Acting Commissioner of Patents and Trademarks